United States Patent
Petit et al.

(10) Patent No.: US 9,647,625 B2
(45) Date of Patent: May 9, 2017

(54) METHOD FOR MANUFACTURING BAW RESONATORS ON A SEMICONDUCTOR WAFER

(71) Applicants: STMicroelectronics SA, Montrouge (FR); STMicroelectronics (Crolles 2) SAS, Crolles (FR)

(72) Inventors: David Petit, Grenoble (FR); Sylvain Joblot, Bizonnes (FR); Pierre Bar, Grenoble (FR); Jean-Francois Carpentier, Grenoble (FR); Pierre Dautriche, Montbonnot (FR)

(73) Assignees: STMICROELECTRONICS SA, Montrouge (FR); STMICROELECTRONICS (CROLLES 2) SAS, Crolles (FR)

( * ) Notice: Subject to any disclaimer, the term of this patent is extended or adjusted under 35 U.S.C. 154(b) by 180 days.

(21) Appl. No.: 14/084,394

(22) Filed: Nov. 19, 2013

(65) Prior Publication Data

US 2014/0075726 A1 Mar. 20, 2014

Related U.S. Application Data

(62) Division of application No. 12/896,382, filed on Oct. 1, 2010, now abandoned.

(30) Foreign Application Priority Data

Oct. 1, 2009 (FR) ...................................... 09 56868

(51) Int. Cl.
*H03H 3/02* (2006.01)
*H03H 9/02* (2006.01)
(Continued)

(52) U.S. Cl.
CPC ................ *H03H 3/02* (2013.01); *H03H 3/04* (2013.01); *H03H 9/0028* (2013.01);
(Continued)

(58) Field of Classification Search
CPC .......... H03H 3/02; H03H 3/04; H03H 9/0028; H03H 9/02102; H03H 9/175; Y10T 29/42;
(Continued)

(56) References Cited

U.S. PATENT DOCUMENTS 4,158,805 A  6/1979  Ballato
4,622,094 A * 11/1986  Otsubo ............. H01J 2237/334
                                                    204/192.32
(Continued)

FOREIGN PATENT DOCUMENTS

EP  1489740 A2  12/2004
FR  2888663 B1  4/2008
(Continued)

OTHER PUBLICATIONS

Lakin et al., "Temperature Compensated Bulk Acoustic Thin Film Resonators," IEEE Ultransonics Symposium, San Juan, PR, Oct. 22-25, 2000, vol. 1, pp. 855-858.
(Continued)

*Primary Examiner* — A. Dexter Tugbang
(74) *Attorney, Agent, or Firm* — Seed IP Law Group LLP

(57) ABSTRACT

A method for manufacturing a wafer on which are formed resonators, each resonator including, above a semiconductor substrate, a stack of layers including, in the following order from the substrate surface: a Bragg mirror; a compensation layer made of a material having a temperature coefficient of the acoustic velocity of a sign opposite to that of all the other stack layers; and a piezoelectric resonator, the method including the successive steps of: a) depositing the compen-
(Continued)

sation layer; and b) decreasing thickness inequalities of the compensation layer due to the deposition method, so that this layer has a same thickness to within better than 2%, and preferably to within better than 1%, at the level of each resonator.

15 Claims, 2 Drawing Sheets

(51) Int. Cl.
    *H03H 3/04*     (2006.01)
    *H03H 9/00*     (2006.01)
    *H03H 9/17*     (2006.01)
    *G02F 1/1337*   (2006.01)
    *G01N 29/02*    (2006.01)

(52) U.S. Cl.
    CPC ........ *H03H 9/02102* (2013.01); *H03H 9/175* (2013.01); *G01N 29/022* (2013.01); *G02F 1/133707* (2013.01); *Y10T 29/42* (2015.01); *Y10T 29/49005* (2015.01); *Y10T 29/49155* (2015.01)

(58) Field of Classification Search
    CPC ........ Y10T 29/49005; Y10T 29/49155; G01N 29/022; G02F 1/133707
    See application file for complete search history.

(56) References Cited

U.S. PATENT DOCUMENTS

| | | | |
|---|---|---|---|
| 5,821,833 A | 10/1998 | Lakin | |
| 5,864,261 A | 1/1999 | Weber | |
| 5,936,150 A * | 8/1999 | Kobrin | G01N 29/022 310/324 |
| 6,297,704 B1 | 10/2001 | Nicholls et al. | |
| 6,342,134 B1 | 1/2002 | Barber et al. | |
| 6,407,649 B1 | 6/2002 | Tikka et al. | |
| 6,998,940 B2 | 2/2006 | Metzger | |
| 7,230,509 B2 | 6/2007 | Stoemmer | |
| 7,235,915 B2 | 6/2007 | Nakamura et al. | |
| 7,408,428 B2 * | 8/2008 | Larson, III | H03H 9/175 310/346 |
| 7,414,350 B1 | 8/2008 | Barber et al. | |
| 7,466,213 B2 | 12/2008 | Lobl et al. | |
| 7,586,390 B2 | 9/2009 | Matsumoto et al. | |
| 7,795,998 B2 | 9/2010 | Mayer et al. | |
| 7,966,722 B2 | 6/2011 | Hart et al. | |
| 8,035,277 B2 | 10/2011 | Barber et al. | |
| 2002/0123177 A1 | 9/2002 | Ruby et al. | |
| 2004/0113720 A1 | 6/2004 | Komuro et al. | |
| 2005/0023932 A1 | 2/2005 | Inoue et al. | |
| 2005/0057117 A1 | 3/2005 | Nakatsuka et al. | |
| 2005/0104690 A1 * | 5/2005 | Larson, III | H03H 9/02102 333/191 |
| 2005/0110598 A1 | 5/2005 | Larson | |
| 2005/0140247 A1 * | 6/2005 | Lee | H03H 3/04 310/320 |
| 2006/0119230 A1 | 6/2006 | Umeda et al. | |
| 2007/0279155 A1 | 12/2007 | Uno et al. | |
| 2008/0246557 A1 * | 10/2008 | Kiwitt | H03H 9/0028 333/133 |
| 2008/0297708 A1 * | 12/2008 | Yang | G02F 1/133788 349/136 |
| 2009/0045703 A1 | 2/2009 | Barber et al. | |
| 2009/0133237 A1 | 5/2009 | Onishi et al. | |
| 2010/0134210 A1 | 6/2010 | Umeda | |
| 2010/0148638 A1 | 6/2010 | Umeda | |
| 2011/0227671 A1 | 9/2011 | Zhang | |

FOREIGN PATENT DOCUMENTS

| | | | |
|---|---|---|---|
| JP | 10-65209 | * | 3/1998 |
| JP | 2005311849 A | | 11/2005 |
| JP | 2006229282 A | | 8/2006 |
| JP | 2006352619 A | | 12/2006 |

OTHER PUBLICATIONS

Ohta et al., "Temperature Characteristics of Solidly Mounted Piezoelectric Thin Film Resonators," IEEE Ultrasonics Symposium, Honolulu, HI, Oct. 5-8, 2003, vol. 2, pp. 2011-2015.

Kobayashi et al., "Fabrication of Piezoelectric Thin Film Resonators with Acoustic Quarter-Wave Multilayers," Jpn. J. Appl. Phys. 41 (2002), pp. 3455-3457.

Reinhardt et al., "Simulation of BAW Resonators Frequency Adjustment," IEEE Ultrasonics Symposium, New York, NY, Oct. 28-31, 2007, pp. 1444-1447.

Mai et al., "Design and Fabrication of ZnO-Based FBAR Microwave Devices for Mobile WiMAX Applications," IEEE Microwave and Wireless Components Letters, Dec. 2007, vol. 17, No. 12, pp. 867-869.

Dossou et al., "60 µW SMR BAW Oscillator Designed in 65nm CMOS Technology," IEEE International Symposium on Circuits and Systems, Seattle, WA, May 18-21, 2008, pp. 1456-1459.

Mourot et al., "Band Reject Filter in BAW Technology," Proceedings of the 38th European Microwave Conference, Amsterdam, the Netherlands, Oct. 27-31, 2008, pp. 349-352.

Petit et al., "Thermally Stable Oscillator at 2.5 GHz Using Temperature Compensated BAW Resonator and its Integrated Temperature Sensor," IEEE International Ultrasonics Symposium, Nov. 2-5, 2008, Beijing, China, pp. 895-898.

Ekeom et al., "Thermoelastic FEM-BEM Model for Solidly Mounted Resonator," IEEE Ultrasonics Symposium, Beijing, China, Nov. 2-5, 2008, pp. 1564-1567.

Petit et al., "Temperature Compensated BAW Resonator and Its Integrated Thermistor for a 2.5GHz Electrical Thermally Compensated Oscillator," IEEE Radio Frequency Integrated Circuits Symposium, Boston, MA, Jun. 7-9, 2009, pp. 339-342.

* cited by examiner

METHOD FOR MANUFACTURING BAW RESONATORS ON A SEMICONDUCTOR WAFER

BACKGROUND

Technical Field

The present disclosure relates to bulk acoustic wave resonators, currently designated as BAW resonators in the art. It is more specifically directed to a method for manufacturing BAW resonators in which a compensation layer, capable of guaranteeing a temperature-stable behavior of its operating frequency, is provided.

Description of the Related Art

A BAW resonator comprises a resonant core, or piezoelectric resonator, formed of two electrodes between which is arranged a layer of a piezoelectric material. When an electric field is applied to the piezoelectric layer by application of a potential difference between electrodes, this results in a mechanical disturbance in the form of an acoustic wave. This wave propagates within the BAW resonator. The fundamental resonance establishes when the acoustic wavelength in the piezoelectric material substantially corresponds to twice the thickness of the piezoelectric layer. Schematically, a BAW resonator behaves as an on switch at the resonance frequency and as an off switch at a so-called antiresonance frequency.

BAW resonators are currently formed above a semiconductor substrate, for example, on a silicon wafer. An acoustic isolation device is then provided between the resonant core and the substrate to avoid a leakage of the acoustic waves into the substrate. There mainly exist two types of BAW resonators: BAW resonators suspended on a membrane and BAW resonators isolated from the substrate by a Bragg mirror.

Suspended BAW resonators, better known as FBARs (Film Bulk Acoustic Wave Resonators) or TFRs (Thin Film Resonators), comprise an isolating air layer between the resonant core and the substrate. Thus, a cavity is provided in the substrate or an air bridge is provided above the substrate. Such resonators have the disadvantage of being difficult to form due to the mechanical fragility of such a device.

BAW resonators with a Bragg mirror, better known as SMRs (Solidly Mounted Resonators), are isolated from the substrate by a reflector, currently a Bragg mirror. They have a stronger structure, better adapted to standard manufacturing methods in microelectronics.

BAW resonators with a Bragg mirror are considered herein.

FIG. 1 is a cross-section view schematically showing a BAW resonator 1 with a Bragg mirror formed on a semiconductor substrate 3. Although FIG. 1 shows a single resonator, in practice, many resonators are formed simultaneously on a same semiconductor wafer.

Resonator 1 comprises a piezoelectric resonator 5 formed of the stacking of a lower electrode 5a, of a layer 5b of a piezoelectric material, and of an upper electrode 5c. As an example, the piezoelectric material may be aluminum nitride (AlN), lead zirconate titanate (PZT), or zinc oxide (ZnO). Electrodes 5a and 5c may be made of molybdenum (Mo), tungsten (W), or aluminum (Al).

An isolation structure 7, for example, a Bragg mirror, forms an interface between piezoelectric resonator 5 and substrate 3. Reflector 7 is an alternated stack of layers 7a of a material with a high acoustic impedance, for example, tungsten (W), and of layers 7b of a material with a low acoustic impedance, for example, silicon oxide ($SiO_2$). The thickness of each layer 7a, 7b is selected to be substantially equal to one quarter of the resonance acoustic wavelength in the material forming it. At the operating frequency, for example, the resonance frequency, the reflector behaves as an acoustic mirror and the waves are confined within the resonator. To obtain a good acoustic isolation, the difference in acoustic impedance between the materials forming layers 7a and 7b must be high. Further, the quality of the acoustic isolation increases along with the number of layers 7a, 7b of the alternated stack.

The methods of deposition of the different layers of resonator 1 do not provide resonance frequencies with the desired accuracy. Substantial variations of the resonance frequency can especially be observed between resonators formed on the same semiconductor wafer.

For this reason, a frequency adjustment layer 9, for example, made of silicon nitride, is provided at a surface of resonator 1. The presence of this layer 9 modifies the behavior of the resonator 1 and especially its operating frequency (for example, the resonance frequency). In a final manufacturing step, a thickness of layer 9 is adjusted by local etching, until the desired frequency is accurately obtained. As an example, an ion etching may be used.

A disadvantage of BAW resonators with a Bragg mirror of the type described in relation with FIG. 1 is the strong dependence of their resonance frequency on temperature. This results from the influence of temperature on the velocity of acoustic waves in the different layers of the resonator 1 and especially in the piezoelectric layer 5b. The temperature coefficient of frequency, or TCF, expresses, in parts per million per degree Celsius (ppm/° C.), the temperature drift of the resonator frequency. In each of the materials forming the resonator 1, the acoustic waves have a certain propagation velocity, and for each material, this propagation velocity has a certain temperature coefficient of velocity, or TCV. All the TCVs of the various materials determine the TCF of the BAW resonator. Generally, the materials of the piezoelectric layers and of the electrodes have a negative temperature coefficient of velocity (TCV). Conversely, materials such as silicon oxide have a positive temperature coefficient of velocity (TCV).

It has been suggested to provide, in the stack of layers forming the BAW resonator, at least one temperature compensation layer having a temperature coefficient of velocity (TCV) of a sign opposite to the TCV of all or of the majority of the other layers, for example, silicon oxide. It is thus attempted to decrease the temperature drift of the BAW resonator, that is, to decrease the absolute value of the TCF.

Several locations have been suggested for the temperature compensation layer, and especially between upper electrode 5c and piezoelectric layer 5b. This layer being placed in the resonance region, it has a strong influence upon the behavior of the resonator. A very small thickness, for example, from 10 to 50 nm, is thus sufficient to provide the desired thermal stabilization behavior. However, a disadvantage of such a layout is that the compensation layer has a significant influence upon the acoustic behavior. This results in a degradation of the quality factor and of the electromechanical coupling of the resonator.

It has also been suggested to provide a compensation layer between upper electrode 5c and frequency adjustment layer 9. A disadvantage of this structure is that the compensation layer makes the step of frequency adjustment by etching of layer 9 more complex. Indeed, the sensitivity of the resonator frequency to the thickness of layer 9 is modified by the presence of the compensation layer. Another disadvantage associated with the provision of this additional layer is the degradation of electric performances, and especially of the electromagnetic coupling and of the quality factor.

In addition to the above-mentioned disadvantages, the above-described temperature compensation modes have the disadvantage of being rather inaccurate. They introduce a strong TCF dispersion in BAW resonators. In particular, substantial variations of the TCF can be observed between BAW resonators manufactured from a same wafer, and all the more from different wafers.

BRIEF SUMMARY

One embodiment of the present disclosure overcomes all or part of the disadvantages of BAW resonators with conventional Bragg mirrors.

One embodiment of the present disclosure is a method for forming a BAW resonator with a Bragg mirror having a frequency response with a better temperature stability than conventional resonators.

One embodiment of the present disclosure is a method enabling to obtain BAW resonators having a temperature behavior with a small dispersion at the scale of a silicon wafer.

One embodiment of the present disclosure is a method which does not degrade the electric performances of the BAW resonator, and especially the electromechanical coupling and the quality factor with respect to conventional resonators, or only slightly does so.

One embodiment of the present disclosure is a method which enables to obtain BAW resonators for which the frequency drift according to temperature is linear.

One embodiment of the present disclosure is a method which is easy to implement.

Thus, an embodiment of the present disclosure provides a method for manufacturing a wafer on which are formed resonators, each resonator comprising, above a semiconductor substrate, a stack of layers comprising, in the following order from a surface of the substrate: a Bragg mirror; a compensation layer made of a material having a temperature coefficient of the acoustic velocity of a sign opposite to that of all the other stack layers; and a piezoelectric resonator, the method comprising the successive steps of: a) depositing the compensation layer; and b) decreasing thickness inequalities of the compensation layer due to the deposition method, so that this layer has a same thickness to within better than 2%, and preferably to within better than 1%, at the level of each BAW resonator.

According to an embodiment of the present disclosure, step b) is carried out by ion etching of overthicknesses due to the deposition method.

According to an embodiment of the present disclosure, the upper layer of the Bragg mirror and the compensation layer form a single layer of a same material.

According to an embodiment of the present disclosure, the compensation layer is made of silicon oxide.

According to an embodiment of the present disclosure, the piezoelectric resonator is formed by the stacking of a lower electrode, of a layer of a piezoelectric material, and of an upper electrode.

According to an embodiment of the present disclosure, the electrodes are made of molybdenum.

According to an embodiment of the present disclosure, the piezoelectric layer is made of aluminum nitride.

According to an embodiment of the present disclosure, the Bragg mirror is formed by the alternated stacking of layers of a material having a first acoustic impedance and of layers of a material having a second acoustic impedance smaller than the first acoustic impedance.

According to an embodiment of the present disclosure, the material having the first acoustic impedance is tungsten and the material having the second acoustic impedance is silicon oxide.

According to an embodiment of the present disclosure, each resonator further comprises, at its surface, a frequency adjustment layer having a thickness capable of compensating for the frequency shift due to manufacturing dispersions.

BRIEF DESCRIPTION OF THE SEVERAL VIEWS OF THE DRAWINGS

The foregoing objects, features, and advantages of the present disclosure will be discussed in detail in the following non-limiting description of specific embodiments in connection with the accompanying drawings.

DETAILED DESCRIPTION

Figure 1:
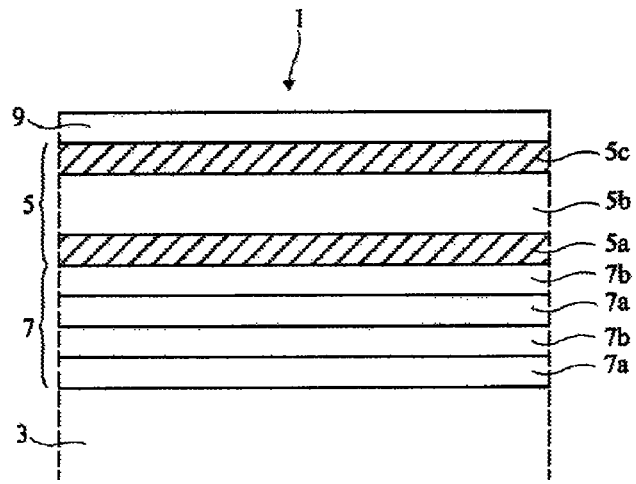
FIG. 1, is a cross-section view schematically showing a known BAW resonator.

For clarity, the same elements have been designated with the same reference numerals in the different drawings and, further, as usual in the representation of microcomponents, the various drawings are not to scale.

Figure 2:
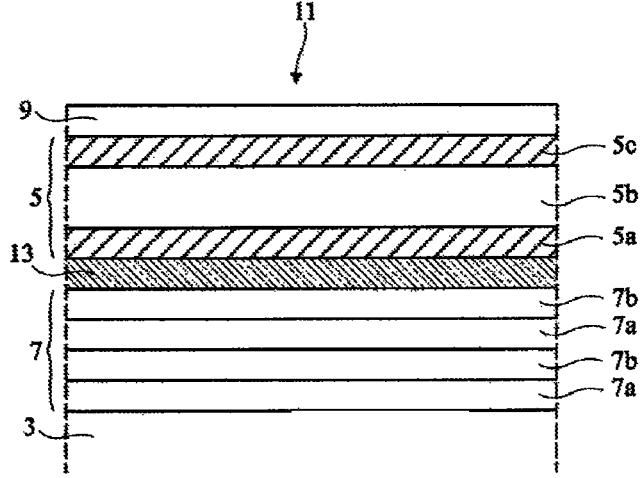
FIG. 2 is a cross-section view schematically showing an example of a temperature-compensated BAW resonator according to an embodiment of the present disclosure.

FIG. 2 is a cross-section view a BAW resonator 11 having a temperature-compensated frequency response according to an embodiment of the present disclosure.

BAW resonator 11 of FIG. 2 is identical to resonator 1 of FIG. 1, but for the fact that a temperature compensation layer 13, for example, made of silicon oxide, is provided between upper layer 7b of reflector 7 and lower electrode 5a.

By analyzing current temperature compensation modes, the present inventors have determined that, among the different layers forming a BAW resonator, the silicon oxide temperature compensation layer 13 is one of the layers with the most inaccurate deposition. As an example, thickness variations on the order of 9% (maximum-minimum) can be observed on this layer, at the scale of a semiconductor wafer, which amounts to a standard deviation on the order of 2%. As a comparison, the thickness variations of piezoelectric layer 5b for example are on the order of 2% (standard deviation on the order of 0.4%) for aluminum nitride.

The inventors have further observed that, among the different layers of BAW resonator 11, silicon oxide layer 13 is that for which thickness variations have the greatest influence upon the resonator TCF. As an example, a thickness variation of 1% of this layer can shift the TCF of the resonator by 0.8 ppm/° C. As a comparison, a thickness variation of 1% of piezoelectric layer 5b only causes a small TCF variation, on the order of 0.2 ppm/° C. Similarly, a thickness variation of 1% of electrodes 5a and 5c causes a TCF variation on the order of 0.1 ppm/° C.

An aspect of an embodiment of the present disclosure is to provide, on manufacturing, a step of leveling of the thickness of temperature compensation layer 13, so that this layer has a constant thickness to within better than 2%

(standard deviation on the order of 0.5%) at the level of each resonator. According to a preferred embodiment of the present disclosure, layer 13 has a same thickness to within better than 1% (standard deviation on the order of 0.2%) at the level of each BAW resonator.

Figure 3:
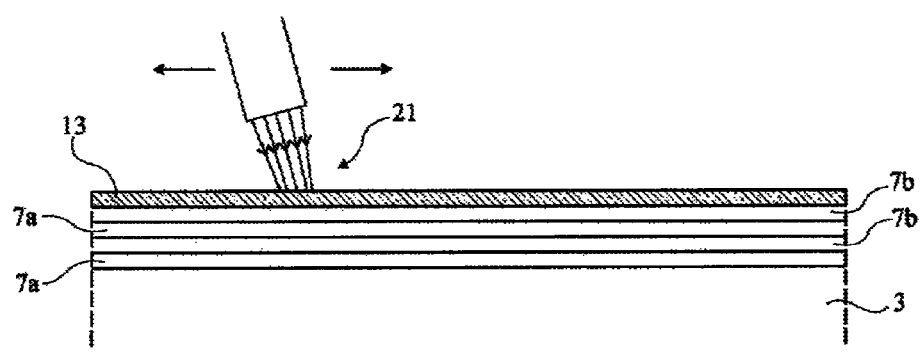
FIG. 3 illustrates a step of an example of a method for forming temperature-compensated BAW resonators of the type described in relation with FIG. 2.

FIG. 3 illustrates a step of an example of a method for forming temperature-compensated BAW resonators of the type described in relation with FIG. 2. FIG. 3 is a cross-section view schematically showing a portion of a semiconductor wafer on which are formed elements 7a, 7b of the Bragg mirror and the temperature compensation layer 13.

After the deposition of the compensation layer 13, a step where the thickness of this layer is made even by etching of the overthicknesses due to the deposition method is provided. This thickness leveling step may advantageously be performed by ion etching, like the final frequency adjustment step described in relation with FIG. 1. As an example, the semiconductor wafer on which the resonators are formed is scanned by an ion beam 21. The scan speed is locally controlled on this wafer to etch the compensation layer more or less strongly. At the end of the leveling step, temperature compensation layer 13 has a same thickness to within better than 2% (standard deviation on the order of 0.5%), and preferably to within better than 1% (standard deviation on the order of 0.2%), at the level of each BAW resonator.

Figure 4A:
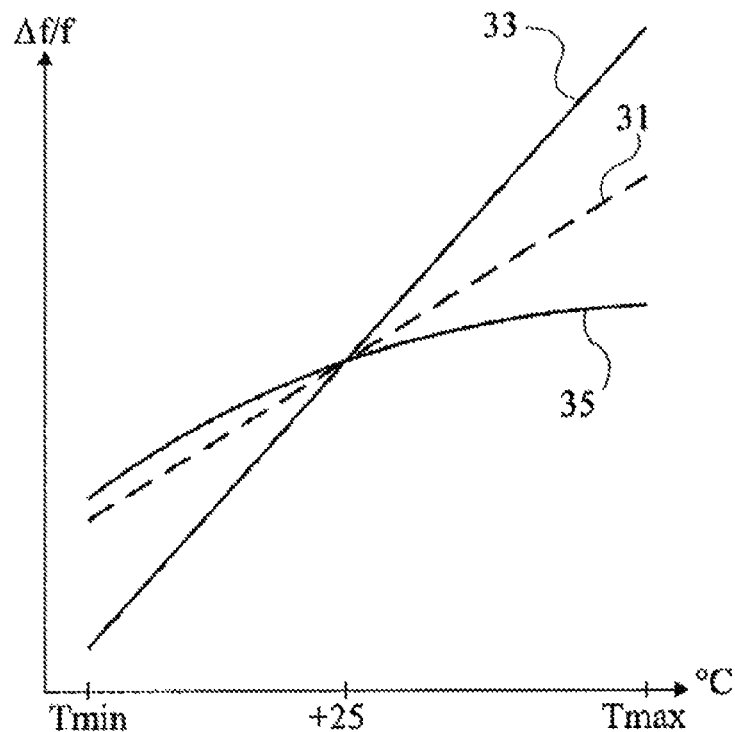
FIGS. 4A and 4B illustrate the variation of the resonance frequency of BAW resonators according to temperature.
Figure 4B:
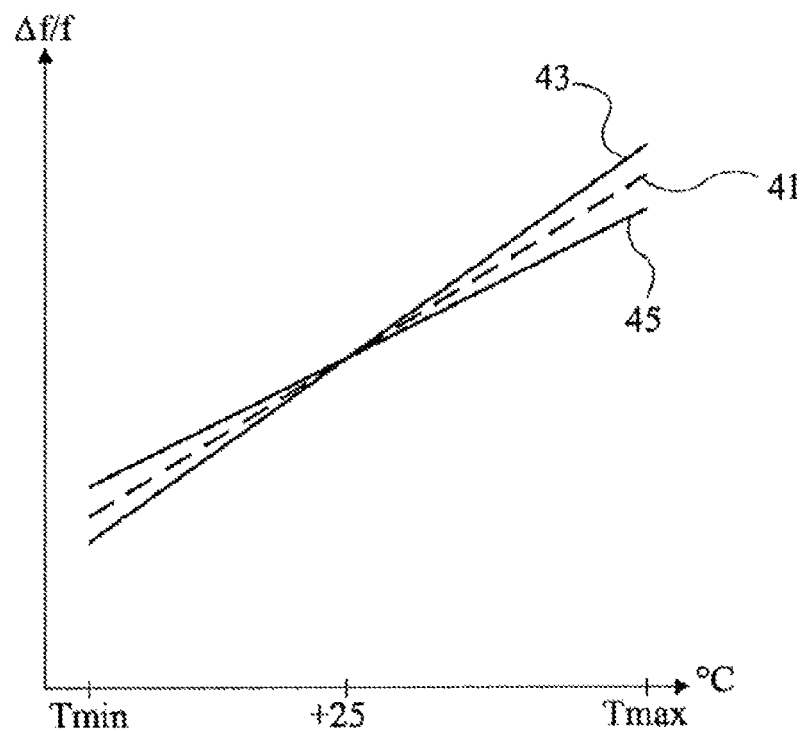

FIGS. 4A and 4B show the variation of frequency drift ($\Delta f/f$) of the BAW resonators, expressed in parts per million (ppm), according to the temperature in the operating temperature range [Tmin, Tmax].

FIG. 4A shows the variation of the frequency drift according to temperature for BAW resonators of the type described in relation with FIG. 2, but for which the step of leveling of the temperature compensation layer has not been carried out. In such resonators, the thickness of temperature compensation layer 13 is tainted with an uncertainty on the order of 9% (standard deviation on the order of 2%).

Curve 31, in dotted lines, shows the ideal temperature behavior, that is, the temperature behavior of a resonator in which the different layers, and especially temperature compensation layer 13, would exhibit no thickness uncertainty.

Curves 33 and 35 illustrate the temperature behavior of two resonators formed from a same semiconductor wafer. Curve 33 for example corresponds to the case of a resonator formed in an area of the semiconductor wafer where the thickness of the temperature compensation layer 13 is maximum. Curve 35 for example corresponds to the case of a resonator formed in an area of the semiconductor wafer where the thickness of the temperature compensation layer 13 is minimum.

Significant differences of the temperature behavior of the resonance frequency can be observed. It can further be observed on curve 35 that for certain resonators, the resonance frequency variation according to temperature is not linear.

FIG. 4B shows the variation of the resonance frequency according to temperature for BAW resonators of the type described in relation with FIG. 2. In such resonators, the thickness of temperature compensation layer 13 exhibits an uncertainty smaller than 2% (standard deviation of 0.5%).

Curve 41, in dotted lines, shows the ideal temperature behavior, that is, the temperature behavior of a resonator in which the different layers, and especially the temperature compensation layer, would exhibit no thickness uncertainty.

Curves 43 and 45 illustrate the temperature behavior of resonators formed from a same semiconductor wafer. Curve 43 for example corresponds to the case of a resonator formed in an area of the semiconductor wafer where the thickness of the temperature compensation layer 13 is maximum. Curve 45 for example corresponds to the case of a resonator formed in an area of the semiconductor wafer where the thickness of the temperature compensation layer 13 is minimum.

It can be observed that the temperature behavior of the operating frequency is substantially the same for all resonators and close to the ideal behavior. It can further be observed that the temperature behavior of the operating frequency is substantially linear across the entire wafer.

Of course, the slopes of the dotted lines and of the tangents to the curves of FIGS. 4A and 4B may be inverted (thus corresponding to a TCF of opposite sign).

An advantage of the provided embodiment is that it enables to obtain a particularly accurate and linear temperature compensation. In particular, it can be observed that resonators manufactured identically on one or several semiconductor wafers have a TCF which is substantially identical and constant in the range of use temperatures of the resonator. Thus, an accurate linear drift of the frequency according to temperature is guaranteed at the scale of a substrate wafer. This especially enables to simplify the steps of calibration of the circuits comprising BAW resonators. This is particularly advantageous in the case of time reference oscillators based on BAW resonators.

Further, if upper layer 7b of the Bragg mirror is made of silicon oxide, it may in practice, advantageously, form one and the same layer with temperature compensation layer 13.

Specific embodiments of the present disclosure have been described. Various alterations and modifications will occur to those skilled in the art. In particular, the present disclosure is not limited to the materials mentioned in the above description. In particular, it is within the abilities of those skilled in the art to implement the desired operation by using other piezoelectric materials, for example, potassium niobate or zinc oxide, and other conductive materials, for example, copper, tungsten, or aluminum to form the resonant core. It will further be within the abilities of those skilled in the art to use other materials having high and low acoustic impedances, for example, silicon nitride or aluminum nitride, capable of forming an isolation reflector between the resonant core and the substrate. Finally, other materials than silicon oxide may be used to form the frequency adjustment and temperature compensation layers, for example, SiON.

Further, the present disclosure is not limited to the use of a local ion beam to make the thickness of the temperature compensation layer even. It will be within the abilities of those skilled in the art to implement the desired operation by using other adapted leveling methods.

Such alterations, modifications, and improvements are intended to be part of this disclosure, and are intended to be within the spirit and the scope of the present disclosure. Accordingly, the foregoing description is by way of example only and is not intended to be limiting.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A method, comprising:
 forming a Bragg mirror on a substrate, the forming of the Bragg mirror including:

forming a first conductive layer having a temperature coefficient of acoustic velocity of a first sign;

forming a compensation layer on the first conductive layer, the compensation layer having a temperature coefficient of acoustic velocity of a second sign that is opposite to that of the first sign; and decreasing thickness inequalities of the compensation layer at least until the compensation layer has a thickness variation less than 2%; and forming a piezoelectric resonator on the compensation layer, the forming of the piezoelectric resonator including:

forming a first electrode on the compensation layer;
forming a piezoelectric layer on the first electrode; and
forming a second electrode on the piezoelectric layer.

2. The method of claim 1 wherein the forming of the Bragg mirror includes:

forming a first dielectric layer on the substrate;
forming the first conductive layer on the first dielectric layer;
forming a second dielectric layer on the first conductive layer; and
forming a second conductive layer on the second dielectric layer.

3. A method, comprising:

forming a stack of layers on a semiconductor substrate, the forming of the stack of layers including:

forming a Bragg mirror on the substrate, the Bragg mirror including:
a first conductive layer on the substrate;
a first dielectric layer on the first conductive layer;
a second conductive layer on the first dielectric layer; and
a second dielectric layer on the second conductive layer, the first and second conductive layers having a temperature coefficient of acoustic velocity (TCV) of a first sign;

depositing a compensation layer on the second dielectric layer of the Bragg mirror, the compensation layer having a TCV of a second sign that is opposite to that of the first sign; and decreasing thickness inequalities of the compensation layer at least until the compensation layer has a thickness variation less than 2%; and forming a piezoelectric resonator on the compensation layer, the forming of the piezoelectric resonator including:

forming a first electrode on the compensation layer;
forming a layer of a piezoelectric material on the lower electrode; and
forming a second electrode on the layer of the piezoelectric material.

4. The method of claim 3 wherein decreasing thickness inequalities includes decreasing the thickness inequalities until at least the compensation layer has less than a 1% variation in thickness.

5. The method of claim 3 wherein decreasing thickness inequalities includes decreasing by ion etching of overthicknesses of the compensation layer caused by the depositing.

6. The method of claim 3 wherein an upper layer of the Bragg mirror and the compensation layer are a single layer of a same material.

7. The method of claim 3 wherein the compensation layer includes silicon oxide.

8. The method of claim 3 wherein the first and second electrodes includes molybdenum.

9. The method of claim 3 wherein the layer of piezoelectric material includes aluminum nitride.

10. The method of claim 3 wherein the first and second conductive layers each have a first acoustic impedance and the first and second dielectric layers each have a second acoustic impedance smaller than the first acoustic impedance.

11. The method of claim 10 wherein the first and second conductive layers are tungsten and the first and second dielectric layers are silicon oxide.

12. The method of claim 3, further comprising forming a frequency adjustment layer on the resonator, the frequency adjustment layer having a thickness capable of compensating for a frequency shift due to manufacturing dispersions.

13. A method, comprising:

forming a Bragg mirror, including:
forming a first dielectric layer on a substrate;
forming a first conductive layer on the first dielectric layer;
forming a second dielectric layer on the first conductive layer; and
forming a second conductive layer on the second dielectric layer;

forming a temperature compensation layer on the second conductive layer of the Bragg mirror; and decreasing thickness inequalities of the temperature compensation aver at east until the compensation layer has a thickness variation less than 2%; and forming a piezoelectric resonator on the temperature compensation layer, the forming the piezoelectric resonator including:

forming a first electrode on the temperature compensation layer;
forming a piezoelectric material layer on the first electrode; and
forming a second electrode on the piezoelectric material layer.

14. The method of claim 13 further comprising forming a frequency adjustment layer on the second electrode of the piezoelectric resonator.

15. The method of claim 13 wherein the temperature compensation layer has a temperature coefficient of acoustic velocity (TCV) of a first sign and the first and second conductive layers of the Bragg mirror have a TCV of a second sign that is opposite to the first sign.

* * * * *

UNITED STATES PATENT AND TRADEMARK OFFICE
CERTIFICATE OF CORRECTION

| | |
|---|---|
| PATENT NO. | : 9,647,625 B2 |
| APPLICATION NO. | : 14/084394 |
| DATED | : May 9, 2017 |
| INVENTOR(S) | : David Petit et al. |

It is certified that error appears in the above-identified patent and that said Letters Patent is hereby corrected as shown below:

In the Claims

Column 8, Lines 36-37:
"compensation aver at east until the compensation layer has" should read, --compensation layer at least until the compensation layer has--.

Signed and Sealed this
First Day of August, 2017

Joseph Matal
*Performing the Functions and Duties of the*
*Under Secretary of Commerce for Intellectual Property and*
*Director of the United States Patent and Trademark Office*